United States Patent [19]
Braun

[11] Patent Number: 5,972,360
[45] Date of Patent: Oct. 26, 1999

[54] SELF-TANNING TOWELETTE

[76] Inventor: Darian Braun, 1821 Dolce Dr., Las Vegas, Nev. 89134

[21] Appl. No.: 09/146,794

[22] Filed: Sep. 3, 1998

[51] Int. Cl.⁶ .............................. A61K 7/00; A61K 7/42; A61K 7/44
[52] U.S. Cl. ............................ 424/401; 424/59; 424/60; 424/400
[58] Field of Search .................................. 424/401, 400, 424/59, 60

[56] References Cited

U.S. PATENT DOCUMENTS 5,514,437  5/1996  Tanner et al. ............................. 424/63
5,679,656  10/1997  Hansenne .................................. 514/54
5,858,334  1/1999  Ascione et al. ........................... 424/59

*Primary Examiner*—Shelley A. Dodson
*Attorney, Agent, or Firm*—Schweitzer Cornman Gross & Bondell LLP

[57] ABSTRACT

A self-tanning product comprising a towelette impregnated with a self-tanning composition. The product provides an inexpensive single-use application which is non-streaking and does not stain the hands. The towel component preferably contains wood pulp fibers to provide an exfoliation effect during application of the tanning solution.

8 Claims, No Drawings

SELF-TANNING TOWELETTE

BACKGROUND OF THE INVENTION

The average person looks upon a tan as a sign of healthy attractiveness and exposure to the outdoors. However, in recent years medical science has come to appreciate the dangers of exposure to the sun, particularly UVA exposure (320–400 nm of the solar spectrum band) and UVB radiation exposure (290–320 nm). There has been a sharp increase in the frequency of cancer occurring in exposed areas, such as basal cell carcinoma, squamous cell carcinoma and, most dangerous of all, malignant melanoma.

The dangers noted above have recently increased the public's interest in self-tanning compositions. In early versions, self-tanning compositions tended to result in an orange-like appearance which most people found unacceptable. However, even present self-tanning compositions can give the user an 'orange' or 'fake' appearance due to the relatively large amount of composition applied onto the hand and thereafter applied to the body part to be treated.

Present self-tanning compositions are sold as liquids, creams and gels. Drops are applied to the user's hand, which then serves to apply the solution to the portion of the body, e.g. face, upper torso, etc. to be "tanned". Streaking of the body portion due to uneven application typically occurs. The texture of the user's hands also factors into this streaking effect. Furthermore, this method generally results in an orange or brown pigment being left on the applicant's hands. The user's hands need to be thoroughly scrubbed to avoid later discoloration.

There is also a certain amount of waste in applying the composition to the hand and then onto the body, as well as maintaining containers or bottles of seldom used solution. Most current self-tanners have been found to leave stains on clothes, furniture, etc. if not given time to dry effectively. Treated body parts must be kept clear of such materials for 0.5 to 1.0 hour after application.

BRIEF DESCRIPTION OF THE INVENTION

The present invention comprises a self-tanning towelette product wherein the towelette cloth has been impregnated with a self-tanning composition typically comprising dihydroxyacetone as the key active ingredient. As in wash-cloths or medical applications, the towelette containing the self-tanning solution is encased in a leakproof foil, typically made of aluminum, silver polyester laminate, or polyester laminate with a foil lining.

As used in the specification and claims, the term "towelette" denotes the well known packet containing a towel cloth impregnated with a liquid and enclosed by a leakproof container, such as a handwash provided at a restaurant The self-tanning composition will additionally contain skin conditioners, emollients and the like. The liquid tanning formula is clear and thus does not result in orange or brown pigment being left on the hands nor in streaking due to the present method of application via towelette. The user need only quickly rinse his hands to avoid discoloration.

In a preferred embodiment, the towelette cloth will contain an appreciable amount of wood pulp fibers so as to provide exfoliation of dead skin during application of the tanning solution. Thus a cleansing effect as well as a tanning effect is obtained.

The compact towelettes or sachets are convenient to have with the user anywhere he may be, e.g. in the glove compartment of the user's car, purse, sports bag, office drawer, etc. Application is simple. The user merely opens the sachet, unfolds the tanning towelette, and wipes it over the body portion, e.g. face, neck or other body part, to have a tanned appearance. A natural glow will develop in one to three hours. For greater tanning, the user can apply another towelette. One application every few days will preserve a tanned appearance.

As compared to large bottles of expensive liquid self-tanners, there is no wastage or having a bottle sit on a shelf for months. Such bottles have a strong odor due to the large amounts of self-tanning agents contained therein whereas the present towelette product has only a light inoffensive smell. The present product is not only inexpensive but offers no waste. It is a single use application. It allows for more uniform application of the self-tanning solution and thus avoids streaking and staining of the hands. A contolled modest application via this towelette can be used to create a "healthy glow" on initial application with a deeper tan produced by repeated application at the user's discretion. Thus the product is more user friendly and can be used to create different effects in a controlled manner by anyone who wants to look healthy.

The combination of a self-tanning solution in a towelette package accordingly offers substantial advantages over the art.

DETAILED DESCRIPTION OF THE INVENTION

The self-tanning composition of the present invention is not, per se, new. The key active ingredient is dihydroxyacetone, which serves as the tanning agent. It normally is preferable to also include ethoxydiglycol to help the tanning agent penetrate into the skin and thus tan faster.

Based on the total weight of self-tanning composition these two ingredients are normally present in the following weight percentage amounts.

|  | Broad Range | Preferred Range |
| --- | --- | --- |
| Dihydroxyacetone | 2.5 to 7.0 | 5 to 6.5 |
| Ethoxydiglycol | 10.0 to 20.0 | 13 to 17.0 |

Other conventional ingredients used in the present solution are the following:

| Ingredient | Purpose | Typical Wt % |
| --- | --- | --- |
| Deionized water | solvent | 60 to 75 |
| Ascorbic acid | antioxidant | 0.1 to 1.0 |
| Butylene Glycol | humectant | 3 to 8 |
| Fragrance oil | fragrance | 0.1 to 0.5 |
| Polysorbate-20 | stabilizer to fragrance | 1 to 5 |
| Propylene glycol and methylparaben/ propylparaben/ | preservatives | 1 to 2 |
| triethylamine | pH adjuster | 0.1 to 0.3 |

The towelette or washing component of the present invention may be various known wiping cloths made of synthetic or natural fibers, e.g. polypropylene, polyethylene terephalate, etc. However, it preferably contains a substantial portion, e.g. 40 to 60, preferably 50 to 60 wt % of wood pulp fibers. It has been found that such a towelette in combination with the above self-tanning solution provides an exfoliation effect on the skin, i.e. it removes undesirable skin flakes or scales. Thus the use of a towelette having a base cloth containing wood pulp fibers is a preferred embodiment of the present invention.

The following example will serve to illustrate the present invention. All parts and percentages in the example and otherwise in the specification are by weight unless otherwise indicated.

EXAMPLE

A self-tanning composition containing the following components was prepared:

| Ingredients: | | |
|---|---|---|
| Active: | | % w/w. |
| Ethoxydiglycol | | 15.000 |
| Dihydroxyacetone | | 6.500 |
| Other: | | |
| 1. | Deionized Water | 66.079 |
| 2. | Butylene Glycol | 5.000 |
| 3. | Cucumber Extract | 2.500 |
| 4. | Polysorbate 20 | 2.000 |
| 5. | Propylene Glycol (and) Diazolidinyl Urea (and) Methylparaben (and) Propylparaben | 1.000 |
| 6. | Fragrance Oil | 0.250 |
| 7. | Ascorbic Acid | 0.500 |
| 8. | Triethanolamine | 0.150 |
| 9. | Tocopheryi Acetate | 0.100 |
| 10. | Tea Tree Oil | 0.100 |
| 11. | Tetrasodium EDTA | 0.500 |
| 12. | Sodium Metabisulfite | 0.200 |
| 13. | FD & C Yellow #5 | 0.013 |
| 14. | FD & C Yellow #6 | 0.008 |

It was then used to impregnate a white towelette of spun laced fabric comprising 45 wt % polyethylene terephthalate and 55 wt % of wood pulp fibers which had a base weight of 2.0 oz/square yard.

The actual impregnation was accomplished as follows: The towel is folded widthwise, cut to length, folded lengthwise and inserted into the film. The film carries the towel to the station where the liquid is applied. While the towel is being carried to the "fill station", the film is sealed on the sides and bottom to create a 3-sided pouch. The liquid is dispensed into the 3 sided pouch, onto and into the towel via a stainless steel nozzle which is in the 3 sided pouch until the film carries the towel to the next station, at which time the "top" or 4th side of the pouch is sealed. Other stations follow. The liquid is sucked out of a drum via a stainless steel pump. The liquid travels in a plastic tubing into the pump. The pump then pumps the liquid into a plastic tube. The liquid travels in this tube to the stainless steel tube which is the nozzle that dispenses the liquid as stated above.

The impregnated solution-cloth was then encased in a polyester laminate packet and all sides sealed to give the desired enclosed towelette product.

Typically the resultant product was a 2.5×4.0 inch packet readily stored for use at the convenience of the purchaser.

As described previously, the towelette is opened and the towel applied to the body to produce a uniform natural looking tan within three hours. The tan can be maintained by repeating the application two to three times weekly. A deeper tan may be achieved by repeated applications.

It is appreciated that various modifications may be made to the present invention without departing from the spirit thereof. That which is sought to be protected is set forth in the following claims.

I claim:

1. A self-tanning product in the form of a towelette comprising a towel impregnated with a self-tanning composition.

2. The self-tanning product of claim 1 wherein said self-tanning composition contains an effective amount of dihydroxyacetone.

3. The self-tanning product of claim 2 wherein said self-tanning composition contains 2.5 to 7.0 weight percent dihydroxyacetone.

4. The self-tanning product of claim 1 wherein said towel contains sufficient wood pulp fibers to provide a skin exfoliation effect during application of the self-tanning composition.

5. The self-tanning product of claim 4 wherein said towel contains 50 to 60 weight percent of wood pulp fibers.

6. The self-tanning product of claim 2 wherein said self-tanning composition further contains a member of the group consisting of skin absorption agents, antioxidants, humectants, preservatives and fragrances.

7. A self-tanning product in the form of a towel impregnated with a self-tanning composition containing an effective amount of dihydroxyacetone and ethoxydiglycol and enclosed in a liquid-proof packet which can readily be opened for one step application to the body and/or face.

8. The product of claim 1 wherein said towel comprises 50 to 60 weight percent wood pulp fibers to provide an exfoliation effect upon application of the self-tanning composition to the skin.

* * * * *